United States Patent [19]

Aoyagi et al.

[11] Patent Number: 4,977,256
[45] Date of Patent: Dec. 11, 1990

[54] METHOD OF ELIMINATING PROTECTIVE GROUPS

[75] Inventors: Sakae Aoyagi; Takaaki Hayashi, both of Shiki; Yasuhiro Kuramoto, Niiza, all of Japan

[73] Assignee: Lederle (Japan), Ltd., Tokyo, Japan

[21] Appl. No.: 205,294

[22] Filed: Jun. 10, 1988

Related U.S. Application Data

[63] Continuation-in-part of Ser. No. 129,560, Dec. 7, 1987, abandoned.

[51] Int. Cl.$^5$ .................. C07D 487/04; C07D 501/04
[52] U.S. Cl. ..................................... 540/227; 540/350
[58] Field of Search ................................ 540/350, 227

[56] References Cited

U.S. PATENT DOCUMENTS 4,429,128 1/1984 Rosati .................................. 540/302

OTHER PUBLICATIONS

Suzuki, Peptide Chemistry, 1976, pp. 45–48 (1977).
Roeske, The Peptides, vol. 3, p. 117 (1981).

Primary Examiner—Robert Gerstl
Attorney, Agent, or Firm—Wegner, Cantor, Mueller & Player

[57] ABSTRACT

A method of deprotection which comprises reacting a compound having at least one of amino, hydroxyl, mercapto and carboxyl groups protected by a substituted or unsubstituted benzyloxycarbonyl group or by a substituted or unsubstituted benzyl group with zinc in a buffer, thereby splitting off the protective benzyloxycarbonyl or benzyl group.

13 Claims, No Drawings

METHOD OF ELIMINATING PROTECTIVE GROUPS

This application is a continuation-in-part application of Ser. No. 129,560, filed Dec. 7, 1987, now abandoned.

BACKGROUND OF THE INVENTION

1. Field of the Invention

This invention relates to a method which comprises reacting a compound having at least one of amino, hydroxyl, mercapto and carboxyl groups protected by a substituted or unsubstituted benzyloxycarbonyl group or by a substituted or unsubstituted benzyl group with zinc in a buffer, thereby splitting off the protective benzyloxycarbonyl or benzyl group.

2. Description of the Prior Art

To avoid undesirable side reactions or decomposition reactions in the production of compounds having an amino group, a hydroxyl group, a mercapto group or a carboxyl group, it is one common practice to protect such a group with a suitable protective group, and split off the protective group after the desired reaction has been performed. A substituted or unsubstituted benzyloxycarbonyl group and a substituted or unsubstituted benzyl group are generally used as the protective groups used for this purpose. Specific examples of frequently used protective groups include a benzyloxycarbonyl group; substituted benzyloxycarbonyl groups such as o-nitrobenzyloxycarbonyl, m-nitrobenzyloxycarbonyl, p-nitrobenzyloxycarbonyl, 2,4-dinitrobenzyloxycarbonyl, 3,4-dinitrobenzyloxycarbonyl, p-chlorobenzyloxycarbonyl, p-bromobenzyloxycarbonyl and p-methoxybenzyloxycarbonyl groups; a benzyl group; and substituted benzyl groups such as o-nitrobenzyl, m-nitrobenzyl, p-nitrobenzyl, 2,4-dinitrobenzyl, 3,4-dinitrobenzyl, p-chlorobenzyl, p-bromobenzyl and p-methoxybenzyl groups.

Elimination of these protective groups may be performed, for example, by treatment with metallic sodium in liquid ammonia, treatment with hydrobromic acid in glacial acetic acid, treatment with hydrochloric acid in alcohol, or catalytic hydrogenation using palladium-carbon or palladium black. The treatment with metallic sodium in liquid ammonia has the defect that the liquid ammonia and metallic sodium are dangerous chemicals. The treatment with hydrochloric acid in alcohol may possibly esterify the carboxyl group which has been split off and become free. In the catalytic hydrogenation, the catalyst is liable to be poisoned with a compound containing sulfur or phosphorus in the reaction system. Furthermore, when the compound to be reacted is a quaternary ammonium salt, this compound itself becomes a catalyst poison, and even under relatively mild deprotecting conditions, the yield of the desired product is frequently decreased considerably.

For example, in the production of carbapenem-series compounds which have aroused interest as antibiotics having strong antibacterial activity, it is the widespread practice to use a starting compound having the carboxyl group at the 3-position protected by a p-nitrobenzyl group and split off the protective group in the final stage to obtain the desired carbapenem compound. But when the compound has a (quaternary ammonium functional group)-alkylthio group as a substituent at the 2-position of the carbapenem skeleton, the quaternary ammonium functional group becomes a catalyst poison, and the yield of the product of the catalytic hydrogenation is only less than 10 and several percent. In view of the fact that the deprotection is generally carried out, in many cases, in a step of obtaining the final compound, the aforesaid treating means resulting in low yields are fatally defective for commercial production.

For example, U.S. Pat. No. 4,644,061 (Bristol-Meyers) discloses a 2-(quaternary ammonium functional group)-alkylthio-carbapenem-4-carboxylate. Example 16 of this U.S. patent illustrates the production of a carbapenem compound having a (2-methyl-1,2,3-thiadiazolium-4-yl)-methylthio group as the (quaternary ammonium functional group)alkylthio group, namely (1R,5S,6S)-2-(2-methyl-1,2,3-thiadiazolium-4-yl)-methylthio-6-[(R)-1-hydroxyethyl]carbapenem-3-carboxylate. This compound can be obtained by catalytic hydrogenation of the corresponding p-nitrobenzyl (1R,5S,6S)-2-[(2-methyl-1,2,3-thiadiazolium-4-yl)-methyl]thio-6-[(R)-1-hydroxyethyl]carbapenem-3-carboxylate in the presence of Pd-C. Its yield, however, is as low as about 4%.

SUMMARY OF THE INVENTION

The present inventors made various investigations in order to remove the aforesaid defects in the elimination reaction of the substituted or unsubstituted benzyloxycarbonyl group or the substituted or unsubstituted benzyl group. These investigations have led to the discovery that by reacting a compound having at least one of amino, hydroxyl, mercapto and carboxyl groups protected by a protective group with zinc in a buffer, the protective group can be split off under mild conditions, and the desired compound can be obtained in good yields.

The present invention thus provides a method of deprotection which comprises reacting a compound having at least one of amino, hydroxyl, mercapto and carboxyl groups protected by a substituted or unsubstituted benzyloxycarbonyl group or by a substituted or unsubstituted benzyl group with zinc in a buffer, thereby splitting off the protective benzyloxycarbonyl or benzyl group.

As one specific embodiment, the present invention further provides a method of producing (1R,5S,6S)-2-[(2-methyl-1,2,3-thiadiazolium-4-yl)methyl]thio-6-[(R)-1-hydroxyethyl]-1-methyl-carbapenem-3-carboxylate, which comprises contacting p-nitrobenzyl (1R,5S,6S)-2-[(2-methyl-1,2,3-thiadiazolium-4-yl)methyl]thio-6-[(R)-1-hydroxyethyl]-1-methyl-carbapenem-3-carboxylate with a zinc powder in the presence of a buffer.

In this method, the pH is preferably in the range of from about 3 to about 9, preferably 5 to 7, most preferably 6 to 7. The buffer is preferably a phosphate or acetate, and the phosphate is more preferred. The concentration of the buffer is preferably from about 0.1 to about 1.0 mole, more preferably from 0.2 to 0.5 mole, especially preferably 0.3 to 0.5 mole. The term "zinc powder" denotes a powder which consists primarily of zinc and may further contain a minor proportion of copper. When copper is included, its amount is at least 1% based on the total amount of the metal powder. The reaction temperature is preferably from about −20° C. to about 50° C., more preferably 0° to 30° C. Most preferably, room temperature is used. An organic solvent should be used in carrying out the reaction. Tetrahydrofuran and acetonitrile are preferred as the organic solvent.

DETAILED DESCRIPTION OF THE INVENTION

The substituted or unsubstituted benzyloxycarbonyl groups and substituted or unsubstituted benzyl groups which can be split off by the method of this invention may be those protective groups for the amino, hydroxyl, mercapto or carboxyl group which have been normally used in peptide chemistry. Specific examples are shown below.

(1) Substituted or unsubstituted benzyloxycarbonyl
Benzyloxycarbonyl,
o-nitrobenzyloxycarbonyl,
m-nitrobenzyloxycarbonyl,
p-nitrobenzyloxycarbonyl,
2,4-dinitrobenzyloxycarbonyl,
3,4-dinitrobenzyloxycarbonyl,
p-chlorobenzyloxycarbonyl,
p-methoxybenzyloxycarbonyl, and
p-bromobenzyloxycarbonyl.

(2) Substituted or unsubstituted benzyl
Benzyl,
o-nitrobenzyl,
m-nitrobenzyl,
p-nitrobenzyl,
2,4-dinitrobenzyl,
3,4-dinitrobenzyl,
p-methoxybenzyl,
p-chlorobenzyl, and
p-bromobenzyl.

The deprotecting method of this invention can be especially preferably applied when the amino or hydroxyl group is protected by a p-nitrobenzyloxycarbonyl group, and the carboxyl group is protected by a p-nitrobenzyl group.

There are a variety of compounds having at least one of amino, hydroxyl, mercapto or carboxyl groups which can be used in this invention.

Amino-containing compounds include, for example, aliphatic amino compounds, aromatic amino compounds, 5- or 6-membered aromatic heterocyclic amino compounds and alicyclic amino compounds. Examples are branched or linear alkanes having an amino group in the molecule, branched or linear alkenes, saturated or unsaturated cycloalkanes, aromatic hydrocarbons, 5- to 6-membered heterocyclic compounds such as furane, thiophene, pyrrole, thiazole, oxazole, thiadiazole, oxadiazole, diazole, pyrazole, triazole, tetrazole, pyridine, pyrimidine and pyridazine, and compounds having such 5- or 6-membered heterocycles bonded within the molecule.

Carboxyl-containing compounds include, for example, aliphatic carboxylic acids, aromatic carboxylic acids, 5- or 6-membered aromatic heterocyclic carboxylic acids, and alicyclic carboxylic acids. Specific examples include the above-exemplified amino-containing compounds in which the carboxyl group is bonded in place of the amino group.

Examples of compounds having a hydroxyl or mercapto group are alcohols, phenols, thiols and thiophenols corresponding to the above exemplified amino-containing compounds and carboxyl-containing compounds.

Compounds having both an amino group and a carboxyl group in the molecule include, for example, amino acids and the above exemplified compounds substituted by both an amino group and a carboxyl group. These compounds may further be substituted by substituents which do not impede the reaction, such as a hydroxyl group, a mercapto group, a halogen atom, an alkyl group, an alkenyl group, a cycloalkyl group, an allyl group and an aralkyl group. The method of this invention is especially effective on cephalosporin compounds and carbapenem compounds containing an amino group and/or a carboxyl group and having a cephem nucleus, a penam nucleus, a penem nucleus, a monobactam nucleus, etc. which are relatively unstable. Specific examples of such compounds are listed below.

7-Amino-3-carbamoyloxymethyl-3-cephem-4-carboxylic acid,
7-[2-(2-aminothiazol-4-yl)-2-(syn)-methoxyiminoacetamide]-3-carbamoyloxymethyl-3-cephem-4-carboxylic acid,
7-[2-(2-aminothiazol-4-yl)-2-(syn)-methoxyiminoacetamide]-3-[(1,2,3-thiadiazol-5-yl)thiomethyl]-3-cephem-4-carboxylic acid,
(1R,5S,6S)-2-[(2-methyl-1,2,3-thiadiazolium-4-yl)methyl]thio-6-[(R)-1-hydroxyethyl]-1-methyl-carbapenem-3-carboxylate,
(1R,5S,6S)-2-[2-(pyridinium-1-yl)ethyl]thio-6-[(R)-1-hydroxyethyl]-1-methyl-carbapenem-3-carboxylate,
(1R,5S,6S)-2-[(1,6-dimethylpyridinium-2-yl)methyl]thio-6-[(R)-1-hydroxyethyl]-1-methyl-carbapenem-3-carboxylate,
(1R,5S,6S)-2-[4-pyrazolidinyl]thio-6-[(R)-1-hydroxyethyl]-1-methyl-carbapenem-3-carboxylic acid, and
(1R,5S,6S)-2-[azetidin-3-yl]thio-6-[(R)-1-hydroxyethyl]-1-methyl-carbapenem-3-carboxylic acid.

It should be understood that the above compounds are only some of the compounds to which the deprotecting method of this invention can be applied, and should not be construed as limiting the invention in any way.

The method of this invention, however, are broadly applied to the synthesis of carbapenem-series compounds, particularly preferably to the production of (1R,5S,6S)-2-[(2-methyl-1,2,3-thiadiazolium-4-yl)methyl]thio-6-[(R)-1-hydroxyethyl]-1-methyl-carbapenem-3-carboxylate having excellent antibacterial activity. This particular compound and its use as an antibacterial agent are disclosed in Japanese Patent Application No. 89012/87 filed on Apr. 11, 1987. This pending Japanese Patent Application discloses (1R,5S,6S)-2-[(2-methyl-1,2,3-thiadiazolium-4-yl)methyl]thio-6-[(R)-1-hydroxyethyl]-1-methyl-carbapenem-3-carboxylate and its use as an antibacterial agent. The entire disclosure of this Japanese Patent Application is incorporated herein by reference.

The deprotecting method of this invention is carried out by reacting a compound having at least one of amino, hydroxyl, mercapto and carboxyl groups protected by a substituted or unsubstituted-benzyloxycarbonyl group or by a substituted or unsubstituted benzyl group with zinc in a buffer.

Examples of preferred buffers include acidic buffers such as a phosphate buffer, an acetate buffer, a citrate buffer and a morpholinopropanesulfonate buffer, and an N-methylmorpholine buffer. The concentration of the buffer is generally 0.1 to 10 moles/liter, preferably 0.2 to 2.0 moles/liter, and more preferably 0.3 to 1.0 moles/liter. In performing the deprotecting reaction, the buffer may be singly used if it at least partially dissovles the compound to be reacted. But in order to secure a homogeneous reaction system, an organic solvent which does not substantially affect the reaction may be used in combination. Examples of the solvent are ethers such as diethyl ether, tetrahydrofuran and dioxane, acetonitrile, dimethylformamide and dimethylacetamide. Tetrahydrofuran and acetonitrile are preferably used.

The pH of the reaction system can be varied depending upon the type of the buffer or the compound to be reacted, and cannot be definitely limited. Generally, the pH is 3 to 9, preferably 5 to 7, and more preferably 6 to 7.

Zinc used in the deprotecting method of this invention may include, for example, elemental zinc in the form of a powder, flower, granule, sand or flake and also a zinc alloy such as a zinc-copper powder and zinc amalgam. For example, copper zinc couple prepared just prior to use by adding a zinc powder to an aqueous solution of copper sulfate, or adding a zinc powder to an acetic acid solution of copper acetate. The amount of zinc used in the method of this invention is not strictly limited. Generally, it is conveniently 1 to 10 parts by weight, preferably 1 to 5 parts by weight, more preferably 1.5 to 2.5 parts by weight, per part by weight of the compound to be reacted.

The reaction temperature and time differ depending upon the type of the compound to be reacted, for example, and is difficult to limit definitely. Usually, it is desirable to perform the reaction at a temperature of −20° to 50° C., preferably 0° to 30° C., more preferably room temperature. At these temperatures, the reaction generally comes to completion in 0.1 to 5 hours.

The reaction in the method of this invention proceeds in good yields under very mild conditions, and the compound obtained by splitting off the protective groups can be isolated and purified by means generally known in organic chemistry, for example by filtration, extraction, crystallization, distillation or chromatography.

The folllowing Examples illustrate the present invention in greater detail. It should be understood that the invention is not limited to these examples.

EXAMPLE I:

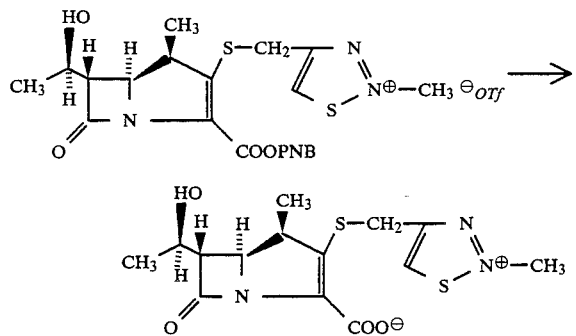

(a) Preparation of p-nitrobenzyl (1R,5S,6S)-2-[(2-methyl-1,2,3-thiadiazolium-4-yl)methyl]thio-6-[(R)-1-hydroxyethyl]-1-methyl-carbapenem-3-carboxylate trifluoromethanesulfonate A mixture of 676 mg of 4-mercaptomethyl-2-methyl-1,2,3-thiadiazolium trifluoromethanesulfonate, 4 ml of methanol and 1 ml of water was cooled to −20° C. To this mixture was added 2 ml of 1N sodium hydroxide solution and the mixture was stirred for a few minutes. To this mixture was added a slut ion of 594 mg of p-nitrobenzyl (1R,5R,6S)- 2-diphenoxyphosphinyl-6-[(R)-1-hydroxyethyl]-1-methylcarbapenem-3-carboxylate in 10 ml of tetrahydrofuran and 8 ml of 0.35M phosphate buffer (pH 7.0) under ice-cooling, and the reaction mixture was stirred for 1 hour at the same temperature to give the above titled compound in the reaction mixture.

This compound was used for the next step without isolation from the reaction mixture.

(b) Preparation of (1R,5S,6S)-2-[(2-methyl-1,2,3-thiadiazolium-4-yl)methyl]thio-6-[(R)-1-hydroxyethyl]-1-methyl-carbapenem-3-carboxylate To the above reaction mixture was added 20 ml of 0.35M phosphate buffer, and a pH of this mixture was adjusted to 6.1 by adding few drops of phosphoric acid. After further addition thereto of 1.2 g of zinc powder, the reaction mixture was stirred for 30 minutes at 18°–20° C., and then filtered using Celite. The organic solvent in the filtrate was removed off under reduced pressure and the resulting residue was washed with 100 ml of ethyl acetate. The aqueous layer was concentrated under reduced pressure and the residue was then adjusted to pH 6.3–6.5. The resulting residue was purified using a Dowex 50W-X4 column with water as an eluent to give 195.4 mg (54.4%) of (1R,5S,6S)-2-[(2-methyl-1,2,3-thiadiazolium-4-yl)methyl]thio-6-[(R)-1-hydroxyethyl]-1-methyl-carbapenem-3-carboxylate after lyophilization.

IR (KBr) cm$^{-1}$: 1750, 1590, 1380.

NMR (CD$_3$OD) δ: 1.16 (3H,d,J=7.0 Hz), 1.24 (3H,d,J=6.0 Hz), 3.12–3.45 (3H,m), 3.98–4.52 (3H,m), 4.63 (3H,s)

EXAMPLE II

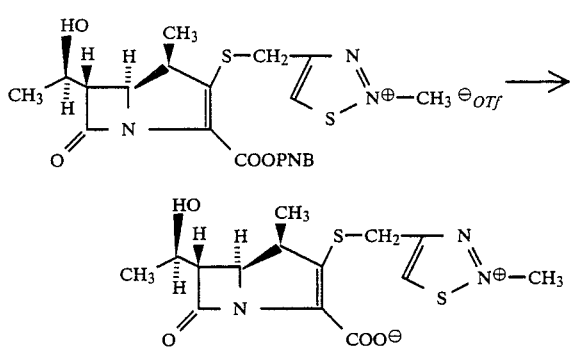

(a) Preparation of p-nitrobenzyl (1R,5S,6S)-2-[(2-methyl-1,2,3-thiadiazolium-4-yl)methyl]thio-6-[(R)-1-hydroxyethyl]-1-methyl-carbapenem-3-carboxylate trifluoromethanesulfonate To a solution of 804 mg of p-nitrobenzyl (1R,5R,6S)-2-diphenoxyphosphinyl-6-[(R)-1-hydroxyethyl]-1-methylcarbapenem-3-carboxylate and 940 mg of 2-methyl-4-tert-butyldiphenylsilylthiomethyl-1,2,3-thiadiazolium trifluoromethanesulfonate in 21 ml of acetonitrile was added dropwise a mixture solution of 1.62 ml of tetrabutylammonium fluoride (1.0M solution in tetrahydrofuran) and 2 ml of tetrahydrofuran at −40° C. under a nitrogen atmosphere. After the dropwise addition, the reaction mixture was stirred for 20 minutes at the same temperature to give the above titled compound. This compound was used for the next step without isolation.

(b) Preparation of
(1R,5S,6S)-2-[(2-methyl-1,2,3-thiadiazolium-4-yl)methyl]thio-6-[(R)-1-hydroxyethyl]-1-methyl-carbapenem-3-carboxylate To the above reaction mixture was added 12 ml of 0.5M phosphate buffer (pH 7.0), 21 ml of water and 1.6 g of zinc powder. Then, the pH of this mixture was adjusted to 6-7 by adding a saturated potassium phosphate solution. After stirring was continued for 20 minutes, the reaction mixture was filtered using Celite and the filtrate was washed with 50 ml of ether. The ether layer was extracted with 50 ml of water and the combined water layers were adjusted to pH 6.8 and concentrated to a smaller volume. The resulting residue was purified using a Dowex 50W-X4 (Na+) column with water as an eluent to give 251 mg (52%) of (1R,5S,6S)-2-[(2-methyl-1,2,3-thiadiazolium-4-yl)methyl]thio-6-[(R)-1-hydroxyethyl]-1-methyl-carbapenem-3-carboxylate after lyophilization.

IR and NMR spectra of this compound showed it to be fully identical with the compound obtained in Example I.

EXAMPLE III

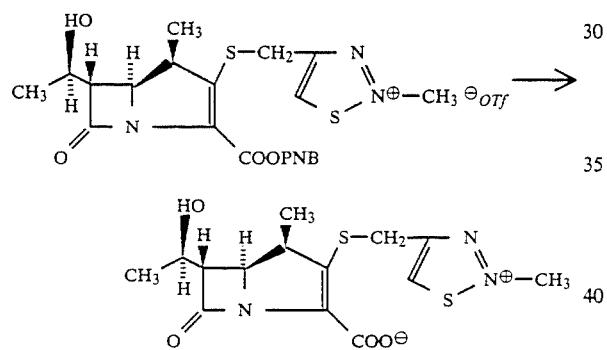

(a) Preparation of p-nitrobenzyl (1R,5S,6S)-2-[(2-methyl-1,2,3-thiadiazolium-4-yl)methyl]thio-6-[(R)-1-hydroxyethyl]-1-methyl-carbapenem-3-carboxylate trifluoromethanesulfonate A mixture of 1.69 g of 4-acetylthiomethyl-2-methyl-1,2,3-thiadiazolium trifluoromethanesulfonate, 10 ml of methanol and 2.5 ml of water was cooled to −20° C. To this mixture was added 5 ml of 1N sodium hydroxide solution and the mixture was stirred for one minute. Then, the mixture was added to a solution of 1.49 g of p-nitrobenzyl (1R,5R,6S)-2-diphenoxyphosphinyl-6-[(R)-1-hydroxyethyl]-1-methyl-carbapenem-3-carboxylate in 5 ml of tetrahydrofuran and 20 ml of 0.35M phosphate buffer (pH 7.0) at 0° C., and the reaction mixture was stirred for 1 hour at the same temperature. After the reaction, the reaction mixture was adjusted to pH 5.8 by adding phosphoric acid and then concentrated under reduced pressure. The resulting residue was purified using a Diaion HP-40 column with water and 20% isopropanol-water as an eluent to give 1.24 g (77.2%) of the above titled compound after lyophilization.

(b) Preparation of
(1R,5S,6S)-2-[(2-methyl-1,2,3-thiadiazolium-4-yl)methyl]thio-6-[(R)-1-hydroxyethyl]-1-methyl-carbapenem-3-carboxylate To a mixture of 640 mg of p-nitrobenzyl (1R,5S,6S)-2-[(2-methyl-1,2,3-thiadiazolium-4-yl)methyl]thio-6-[(R)-1-hydroxyethyl]-1-methyl-carbapenem-3-carboxylate trifluoromethanesulfonate, 10 ml of tetrahydrofuran and 20 ml of 0.35M acetate buffer (pH 5.0) was added 5 g of zinc powder at 0° C., and the reaction mixture was stirred for 1 hour at the same temperature. After the reaction, the reaction mixture was filtered using Celite and the filtered layer was washed with ether. The aqueous layer was cencentrated under reduced pressure and the resulting residue was purified using a Dowex 50W-X4 column with water as an eluent to give 179 mg (50.4%) of (1R,5S,6S)-2-[(2-methyl-1,2,3-thiadiazolium-4-yl)methyl]thio-6-[(R)-1-hydroxyethyl]-1-methyl-carbapenem-3-carboxylate after lyophilization.

IR and NMR spectra of this compound showed it to be fully identical with the compound obtained in Example I.

EXAMPLE IV

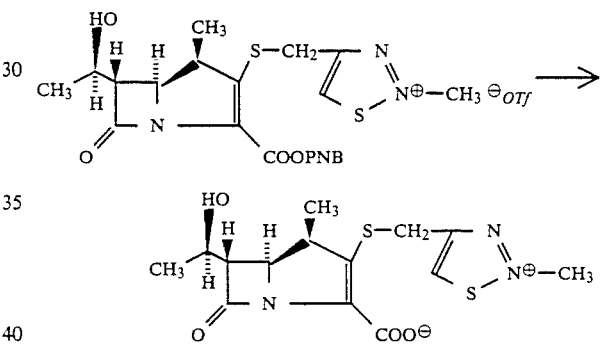

To a solution of 640 mg of p-nitrobenzyl (1R,5R,6S)-2-[(2-methyl-1,2,3-thiadiazolium-4-yl)methyl]thio-6-[(R)-1-hydroxyethyl]-1-methyl-carbapenem-3-carboxylate trifluoromethanesulfonate obtained in Example III, (a) in 10 ml of tetrahydrofuran and 20 ml of 0.35M phosphate buffer (pH 6.6) was added copper-zinc couple (prepared from 300 mg of anhydrous copper sulfate in 10 ml of water and 1.5 g of zinc powder), and the reaction mixture was stirred for 1 hour at room temperature. After the reaction, the reaction mixture was filtered using Celite and the resulting filtrate was treated in the same manner as described in Example III, (b) to give 158 mg (44.5%) of (1R,5S,6S)-2-[(2-methyl-1,2,3-thiadiazolium-4-yl)methyl]thio-6-[(R)-1-hydroxyethyl]-1-methyl-carbapenem-3-carboxylate IR and NMR spectra of this compound showed it to be fully identical with the compound obtained in Example I.

EXAMPLE V

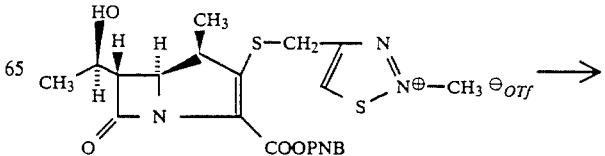

-continued

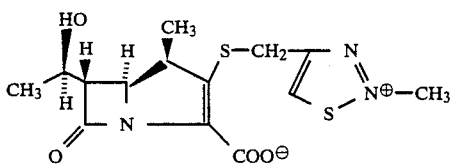

(a) Preparation of p-nitrobenzyl (1R,5S,6S)-2-[(2-methyl-1,2,3-thiadiazolium-4-yl)methyl]thio-6-[(R)-1-hydroxyethyl]-1-methyl-carbapenem-3-carboxylate trifluoromethanesulfonate A mixture of 338 mg of 4-acetylthiomethyl-2-methyl-1,2,3-thiadiazolium trifluoromethanesulfonate, 2 ml of methanol and 0.5 ml of water was cooled to $-20°$ C. To this mixture was added 1 ml of 1N sodium hydroxide solution and the mixture was stirred for a few minutes. To this mixture was added a solution of 298 mg of p-nitrobenzyl (1R,5R,6S)-2-diphenoxyphosphinyl-6-[(R)-1-hydroxyethyl]-1-methylcarbapenem-3-carboxylate in 5 ml of tetrahydrofuran and 4 ml of 0.35M phosphate buffer (pH 7.0) under ice-cooling, and the reaction mixture was stirred for 1 hour at the same temperature to give the above titled compound in the reaction mixture.

This compound was used for the next step without isolation from the reaction mixture.

(b) Preparation of (1R,5S,6S)-2-[(2-methyl-1,2,3-thiadiazolium-4-yl)methyl]thio-6-[(R)-1-hydroxyethyl]-1-methyl-carbapenem-3-carboxylate To the above reaction mixture was added a mixture solution of 11 ml of 0.35M phosphate buffer and 10 ml of n-butanol, and the pH of the mixture was adjusted to 6.1 by adding few drops of phosphoric acid. After further addition thereto of 600 mg of zinc powder, the reaction mixture was stirred for 50 minutes at room temperature, and then filtered using Celite. The filtrate was washed with ethyl acetate and the aqueous layer was concentrated under reduced pressure. The resulting residue was purified using a Dowex 50W-X4 column with water as an eluent to give 195.4 mg (54.4%) of (1R,5S,6S)-2-[(2-methyl-1,2,3-thiadiazolium-4-yl)methyl]thio-6-[(R)-1-hydroxyethyl]-1-methyl-carbapenem-3-carboxylate after lyophilization.

IR and NMR spectra of this compound showed it to be identical with the compound obtained in Example I.

EXAMPLE VI

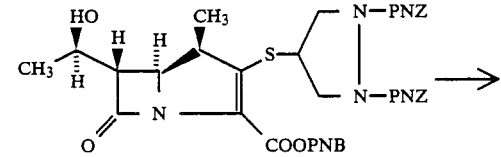

To a mixture of 200 mg of p-nitrobenzyl (1R,5S,6S)-6-[(R)-1-hydroxyethyl]-1-methyl-2-[N,N'-di(p-nitrobenzyloxycarbonyl)pyrazolidin-4-yl]thio-2-carbapenem-3-carboxylate, 3 ml tetrahydrofuran and 9 ml of 0.35M phosphate buffer (pH 5.8) was added 600 mg of the zinc powder, and the reaction mixture was stirred for 2 hours at room temperature. After the reaction, the reaction mixture was filtered using Celite and then the filtrate was adjusted to pH 5.5 and washed with ether. The aqueous layer was concentrated under reduced pressure and the resulting residue was purified using a HP-40 column with water as an eluent to give 47 mg (60.5%) of (1R,5S,6S)-2-(4-pyrazolidin-4-yl)thio-6-[(R)-1-hydroxyethyl]-1-methyl-carbapenem-3-carboxylic acid after lyophilization.

IR (KBr) cm$^{-1}$: 1750
NMR (D$_2$O-CD$_3$OD) δ: 1.23 (3H, d,J=6.0 Hz), 1.40 (3H,d, J=7.0 Hz), 3.3–4.4 (9H,m)

EXAMPLE VII

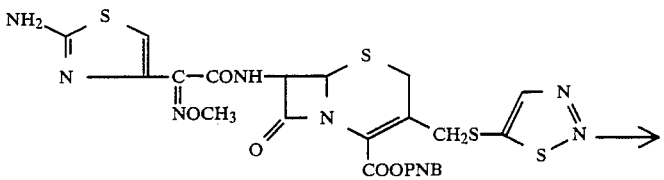

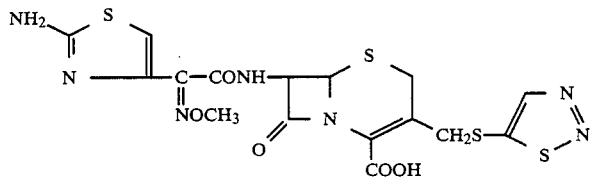

To a mixture of 500 mg of p-nitrobenzyl 7β-[2-(2-aminothiazol-4-yl)-(Z)-2-methoxyiminoacetamide]-3-[(1,2,3-thiadiazol-5-yl)thiomethyl]ceph-3-em-4-caboxylate, 7 ml of tetrahydrofuran and 7 ml of 0.35M phosphate buffer (pH 6.1) was added 5 g of zinc powder, and the reaction mixture was stirred for 30 minutes at room temperature. After the reaction, undissolved substances were removed by using Celite, and the pH of the filtrate was adjusted to an acidic side by adding dilute hydrochloric acid. The resulting precipitate was collected and dissolved in 0.1N sodium hydroxide solution. This solution was adjusted to pH 5.5, and purified using HP-40 column with water and water-isopropanol (9:1) as an eluent to give 322 mg (78%) of 7β-[(2-aminothiazol-4- yl)-(Z)-2-methoxyiminoacetamide]-3-[(1,2,3-thiadiazol-5-yl)thiomethyl]ceph-3-em-4-carboxylic acid after lyophilization.

IR and NMR spectra of this compound agreed with those of the authentic compound.

EXAMPLE VIII

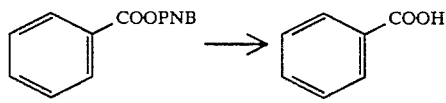

To a solution of 160 mg of p-nitrobenzyl benzoate in 5 ml of tetrahydrofuran and 5 ml of 0.35M phosphate buffer (pH 6.1) was added 1.6 g of zinc powder and the mixture was stirred for 3 hours at room temperature. After the reaction, the reaction mixture was filtered using Celite, and the pH of the filtrate was adjusted to an alkaline side by adding sodium carbonate. It was then washed with 10 ml of ethyl acetate twice. The aqueous layer was acidified and then extracted with ethyl acetate (10 ml×3). The organic layer was washed with water and dried over magnesium sulfate. The solvent was removed under reduced pressure and the residue was purified by chromatography to give 58 mg (76.4%) of benzoic acid. m.p. 121°–122° C.

This compound was identified as the authentic compound by comparison of the IR and NMR spectra.

EXAMPLE IX

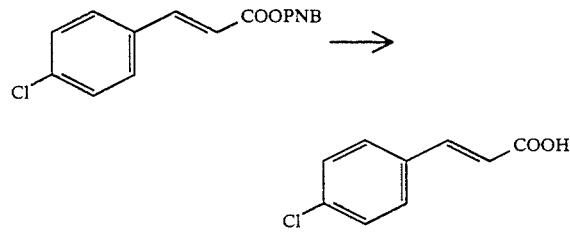

53 mg (92.2%) of 4-chlorocinnamic acid was obtained from 100 mg of p-nitrobenzyl 4-chlorocinnamate, 4 ml of tetrahydrofuran, 4 ml of 0.35M phosphate buffer (pH 6.1) and 1 g of zinc powder in the same manner as described in Example 8. m.p. 246°–248° C.

The IR spectral data of this compound agreed with those of the authentic compound.

EXAMPLE X

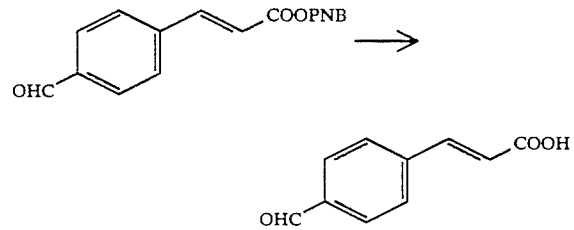

105 mg (92.8%) of 4-formylcinnamic acid was obtained from 200 mg of p-nitrobenzyl 4-formylcinnamate, 7 ml of tetrahydrofuran, 7 ml of 0.35M phosphate buffer (pH 6.1) and 2 g of zinc powder in the same manner as described in Example 8. m.p. 250°–252 ° C. (decomp.).

This compound was identified as the authentic compound by comparison of the IR and NMR spectra.

EXAMPLE XI

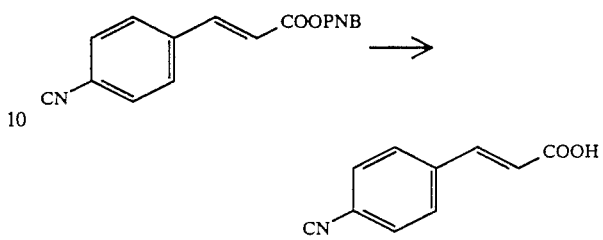

4-Cyanocinnamic acid was obtained in 92.6% yield from p-nitrobenzyl 4-cyanocinnamate in the same manner as described in Example 8. m.p. 180° C.

EXAMPLE XII

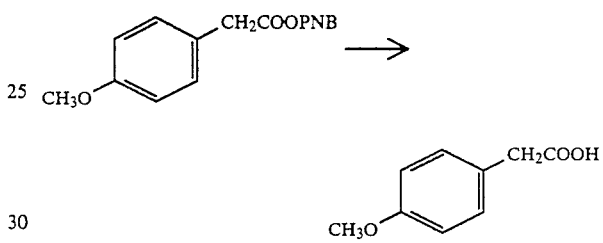

4-Methoxyphenylacetic acid was obtained in 92.6% yield from p-nitrobenzyl 4-methoxyphenylacetate in the same manner as described in Example 8. m.p. 85°–86° C.

EXAMPLE XIII

To a solution of 270 mg of 4-methyl-5-p-nitrobenzyloxycarbonyl-1,2,3-thiadiazole in 7 ml of tetrahydrofuran and 7 ml of 0.35M phoshate buffer (pH 6.1) was added 2.7 g of zinc powder, and the reaction mixture was stirred for 4 hours at room temperature. After the reaction, the reaction mixture was filtered using Celite and the filtrate was rendered alkaline by adding sodium carbonte and washed with ethyl acetate. The aqueous layer was then acidified by hydrochloric acid and extracted with ethyl acetate. The organic layer was washed with water, dried over magnesium sulfate, the solvent was removed under reduced pressure. The resulting residue was purified using silica gel column chromatography to give 120 mg (91.0%) of 4-methyl-5-hydroxycarbonyl-1,2,3-thiadiazole. m.p. 190° C.

This compound was identified with the authentic sample by comparison of the IR spectra.

REFERENCE EXAMPLE

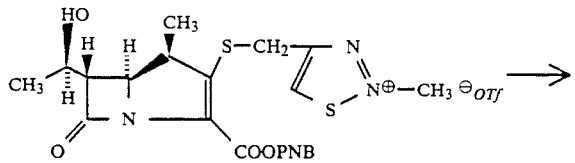

-continued

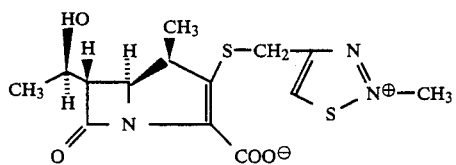

257 mg of p-nitrobenzyl (1R,5S,6S)-2-[(1,2,3-thiadiazol-4-yl)methyl]thio-6-[(R)-1-hydroxyethyl]-1-methylcarbapenem-3-carboxylate was dissolved in 4.0 ml of dichloromethane, and the solution was cooled with ice to 0° C. After dropwise addition of 0.073 ml of methyl trifluoromethanesulfonate, the mixture was stirred at 0° C. for 18 hours. To this solution were added 5.0 ml of a 0.5M N-methylmorholineHCl buffer solution (pH 6.8), 4.4 ml of n-butanol and 4.0 ml of ethyl acetate in this order. After further addition of mg of a 20% palladium hydroxide-carbon, catalytic hydrogenation was carried out at room temperature for 2 hours under 3.0 atmospheres. The reaction mixture was filtered using Celite. After the Celite was washed with small amounts of methanol and water, the filtrate was collected and washed with ether. The aqueous layer was then concentrated under reduced pressure and purified using a Dowex 50W-X4 (Na+) column to give 22.6 mg (11.8%) of (1R,5S,6S)-2-[(2-methyl-1,2,3-thiadiazolium-4-yl)methyl] thio-6-[(R)-1-hydroxyethyl]-1-methyl-carbapenem-3-carboxylate after lyophilization.

IR and NMR spectra of this compound showed it to be fully identical with the compound obtained in Example 1.

What we claim is:

1. A method deprotection which comprises contacting a β-lactam compound having at least one of an amino or carboxyl group protected by a p-nitrobenzyloxycarbonyl group or a p-nitrobenzyl respectively group with zinc powder in a buffer selected from the group consisting of a phosphate buffer, an acetate buffer, a citrate buffer, an N-methylmorphorine buffer, and a morpholinopropanesulfonate buffer having a pH in the range of from 5 to 7 whereby splitting off said protective p-nitrobenzyloxycarbonyl or p-nitrobenzyl group.

2. A method of claim 1 wherein the β-lactam compound is a compound selected from the group consisting of cephalosporin compounds and carbapenem compounds containing an amino group and/or a carboxyl group.

3. A method of claim 1 wherein the concentration of the buffer is from about 0.1 to about 10.0 molar.

4. The method of claim 3 wherein the concentration of the buffer is from 0.2 to 2.0 molar.

5. A method of claim 1 wherein the contacting is carried out at a temperature of from about −20° C. to about 50° C.

6. A method of producing (1R,5S,6S)-2-[(4-pyrazolidin-4-yl)thio-6-[(R)-1-hydroxyethyl]-1-methyl-carbapenem-3-carboxylic acid, which comprises contacting p-nitro-benzyl(1R,5S,6S)-6-[(R)-1-hydroxyethyl]-1-methyl-2-[(N,N'-di(p-nitro-benzyloxycarbonyl)-pyrazolidin- 4-yl]thio-2-carbapenem-3-carboxylate with a zinc powder in the presence of a buffer selected from a phosphate buffer or an acetate buffer having a pH in the range of from 5.0 to 7.0.

7. A method of producing 7β-[2-(2-amino-thiazol-4-yl)-(Z)-2-methoxyiminoacetamide]-3-(1,2,3-thiadiazol-5-yl)thiomethyl]-ceph-3-em-4-carboxylic acid, which comprises contacting p-nitrobenzyl 7β-[2-(2-amino-thiazol-4-yl)-(Z)-2-methoxyiminoacetamide]-3-[(1,2,3-thiadiazol-5-yl)thiomethyl]-ceph-3-em-4-carboxylate with a zinc powder in the presence of a buffer selected from a phosphate buffer or an acetate buffer having a pH in the range of from 5 to 7.

8. A method of producing (1R,5S,6S)-2-[(2-methyl-1,2,3-thiadiazolium-4-yl)methyl]thio-6-[(R)-1-hydroxyethyl]-1-methyl-carbapenem-3-carboxylate, which comprises contacting p-nitrobenzyl (1R,5S,6S)-2-[(2-methyl-1,2,3-thiadiazolium-4-yl)methyl]thio-6-[(R)-1-hydroxyethyl]-1-methyl-carbapenem-3-carboxylate with a zinc powder in the presence of a buffer selected from a phosphate buffer or an acetate buffer having pH in the range from 5 to 7.

9. A method of claim 8 wherein the zinc powder consists essentially of zinc.

10. A method of claim 8 wherein the zinc powder consists primarily of zinc and at least one percent of copper.

11. A method of claim 8 wherein the concentration of the buffer is from about 0.1 to about 10.0 moles.

12. The method of claim 11 wherein the concentration of the buffer is from 0.2 to 2.0 moles.

13. A method of claim 8 wherein the contacting is carried out at a temperature of from about −20° C. to about 50° C.

* * * * *